(12) United States Patent
Pollmann

(10) Patent No.: US 9,599,553 B2
(45) Date of Patent: Mar. 21, 2017

(54) TESTING OF QUALITY OF COOKING OIL

(71) Applicant: Daniel Pollmann, St. Louis, MO (US)

(72) Inventor: Daniel Pollmann, St. Louis, MO (US)

(73) Assignee: Bunge North America, Inc., St. Louis, MO (US)

( * ) Notice: Subject to any disclaimer, the term of this patent is extended or adjusted under 35 U.S.C. 154(b) by 62 days.

(21) Appl. No.: 14/671,159

(22) Filed: Mar. 27, 2015

(65) Prior Publication Data

US 2016/0282261 A1    Sep. 29, 2016

(51) Int. Cl.
  *G01N 21/27*    (2006.01)
  *G01N 33/28*    (2006.01)

(52) U.S. Cl.
  CPC .......... *G01N 21/274* (2013.01); *G01N 33/28* (2013.01)

(58) Field of Classification Search
  CPC ...................................................... G01J 3/524
  USPC ...................................................... 356/243.5
  See application file for complete search history.

(56) References Cited

U.S. PATENT DOCUMENTS

| | | | | |
|---|---|---|---|---|
| 5,818,731 A * | 10/1998 | Mittal | ................ | A47J 37/1266 702/22 |
| 8,699,019 B2 * | 4/2014 | Wang | ................ | G01N 33/03 356/301 |
| 2005/0036668 A1 * | 2/2005 | McLennan | ........... | G06K 9/4652 382/128 |
| 2008/0041238 A1 * | 2/2008 | Usui | ................... | A47J 37/1257 99/408 |
| 2012/0086942 A1 * | 4/2012 | Honda | ................... | G01N 21/27 356/436 |
| 2013/0322750 A1 * | 12/2013 | Agarwal | ............. | G06K 9/4652 382/165 |
| 2016/0069856 A1 * | 3/2016 | Gorritxategi | ...... | G01N 15/0227 356/70 |
| 2016/0161463 A1 * | 6/2016 | Onuma | .................. | G01N 21/27 356/70 |

* cited by examiner

*Primary Examiner* — Kara E Geisel
*Assistant Examiner* — Shawn Decenzo
(74) *Attorney, Agent, or Firm* — Jones Day

(57) ABSTRACT

This relates to a processor-implemented method of providing an oil-quality indication. The method includes receiving image data associated with a captured image, wherein the image includes (i) oil sample pixels associated with an oil sample and (ii) calibration color pixels associated with a calibration color. The oil sample pixels are adjusted based on the calibration color pixels. A saturation value and a hue value are determined based on the adjusted oil sample pixels. An oil quality value is determined based on the saturation value and the hue value. The oil quality value is stored in a processor-readable medium.

48 Claims, 8 Drawing Sheets

TESTING OF QUALITY OF COOKING OIL

TECHNICAL FIELD

This relates to a test method for determining amount of degradation in cooking oil.

BACKGROUND

Cooking oil used in frying degrades with use. One method of determining the amount of degradation is ISO 8420. This test method determines extent of degradation as a function of polarity, which is indicative of amount of polar compounds that form in the oil over time due to frying.

SUMMARY

This relates to a processor-implemented method of providing an oil-quality indication. The method includes receiving image data associated with a captured image, wherein the image includes (i) oil sample pixels which are associated with an oil sample and (ii) calibration color pixels which are associated with a calibration color. The oil sample pixels are adjusted based on the calibration color pixels. A saturation value and a hue value are determined based on the adjusted oil sample pixels. An oil quality value is determined based on the saturation value and the hue value. The oil quality value is stored in a processor-readable medium.

DETAILED DESCRIPTION

Figure 1:
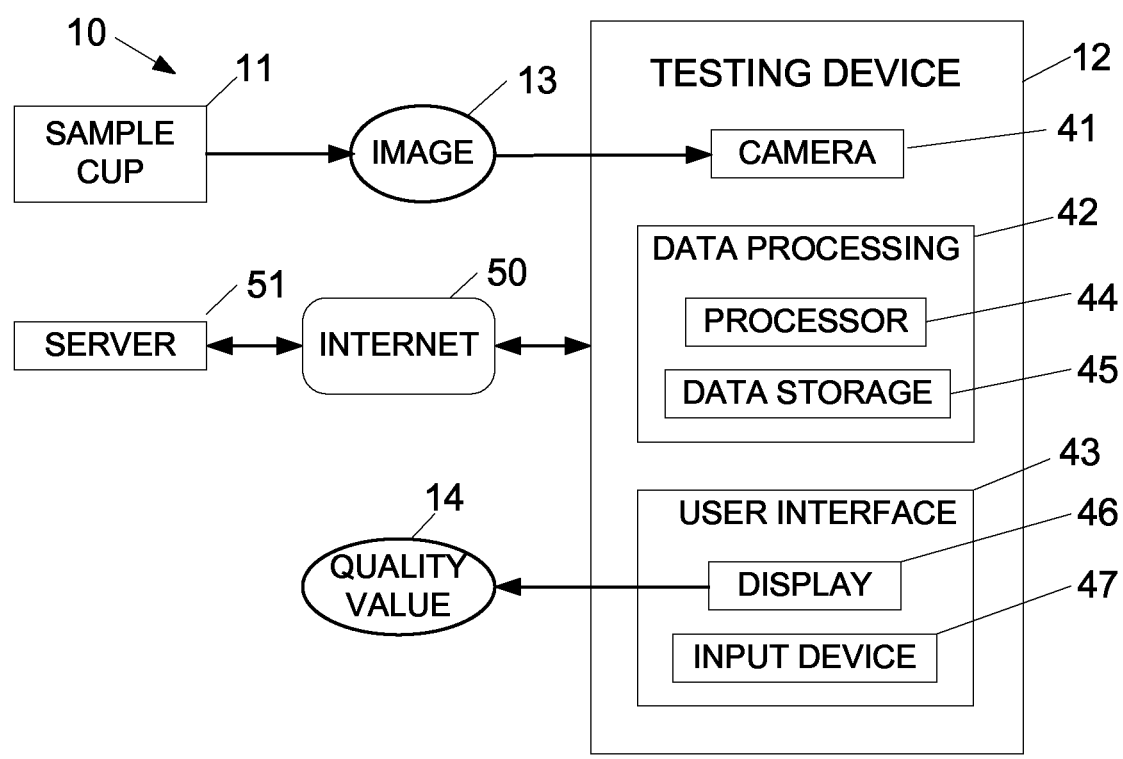
FIG. 1 is a block diagram of an apparatus for determining quality of oil.
Figure 2A:
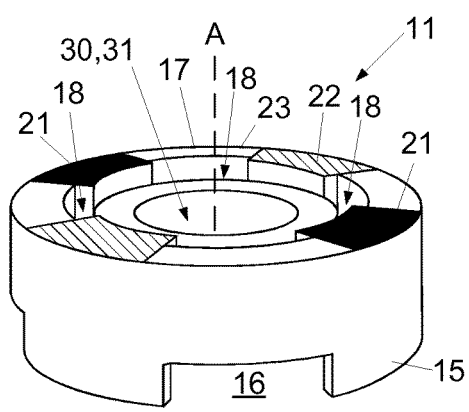
FIG. 2A is a perspective view of a sample cup of the apparatus.
Figure 2B:
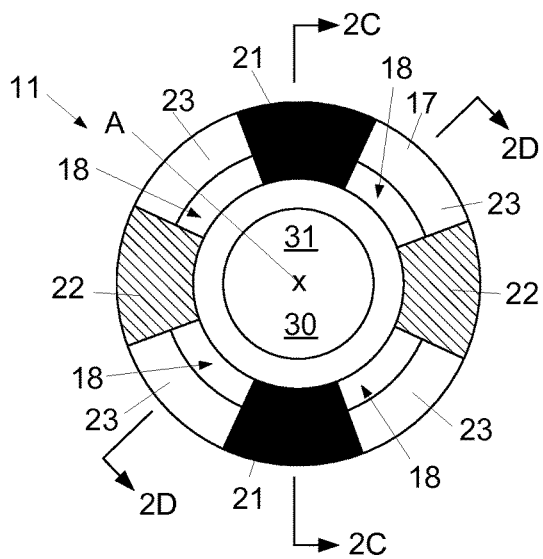
FIG. 2B is a top view of the sample cup.
Figure 2C:
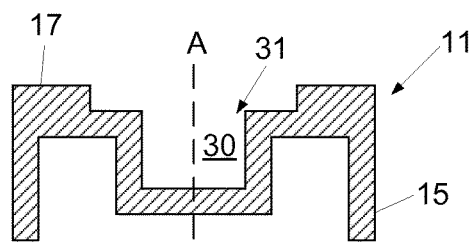
FIG. 2C is a sectional view taken at line 2C-2C of FIG. 2B.
Figure 2D:
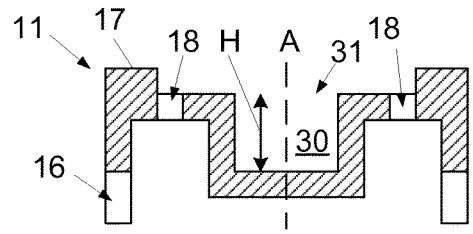
FIG. 2D is a sectional view taken at line 2D-2D of FIG. 2B.

FIG. 1 is a block diagram of an apparatus 10 for determining quality of oil. The apparatus includes (i) a sample cup 11 that holds a sample of oil to be tested and (ii) an electronic testing device 12. The testing device 12 captures an image 13 (picture) of the oil sample, processes pixels of the image, determines quality of the oil based on hue and saturation of the pixels, and outputs (reports) an indication 14 of the oil's quality.

An example of the oil to be tested is oil used in frying food. And the determined quality relates degradation of the oil due to frying.

An example of the sample cup 11 (container) is shown in FIGS. 2A-2D. The cup 11 has a cylindrical periphery (circumferential surface) and is symmetric about a central axis A. The cup 11 has, at its bottom, four feet 15 configured to rest on a table. The feet 15 are circumferentially spaced apart by four openings 16.

The cup 11 in FIGS. 2A-2D has a top surface 17 with areas (sections, spots, patches, strips) of different calibration colors, in this case two black areas 21 and two gray areas 22 separated by four white areas 23. The colored areas 21, 22, 23 may be formed by (i) starting out with the cup 11 having a substantially white surface, (ii) coating radially-opposite first and second sections of the top surface 17 with black color, and (iii) coating radially-opposite third and fourth sections of the top surface with a gray color, and (iv) leaving four sections, between the other colored sections, uncoated and thus white. Accordingly, relative to an angular scheme with one of the black sections at 0°: The two black areas 21 are centered at 0° and 180°, the two gray areas 22 are centered at 90° and 270°, and the four white areas 23 are centered at 45°, 135°, 225° and 315°. The colored areas 21, 22, 23 may have equal circumferentially extending widths. The black and gray areas 21, 22 might be formed by painting or marking with paint or ink, or by adhering strips of black and gray tape to the cup's top surface. The white areas 23 may be formed with white paint, white ink, or white tape, or by leaving the white cup surface 17 uncoated. All of the colored areas may be contained on the surface of a single ring-shaped piece of tape adhered to the top surface 17 of the cup 11.

The sample cup 11 in FIGS. 2A-2D has four drain holes 18 (channels) extending downward from the top surface 17. Each drain hole 18 is located circumferentially between a black area 21 and a gray area 22. Each drain hole 18 is, further, located radially inward from, and circumferentially aligned with, a corresponding white area 23.

The cup 11 in FIGS. 2A-2D has a well 30 (cavity; pocket) that extends downward from a round top opening 31 in the top surface 17. The well 30 is generally cylindrical and centered on the axis A. The well 30 is configured to hold a sample of the oil to be tested.

The testing device 12 in this example includes (i) an image capture module 41 (digital camera) for capturing an image of the cup with the oil sample, (ii) a data processing module 42 for processing pixel data from the image to determine an oil quality indication, and (iii) a user interface 43 for communicating with a user.

The data processing device 42, in this example, includes a processor 44. The data processing device 42 further includes a non-transient processor-readable data storage medium 45, such as a hard drive or solid state memory. The storage medium may store data (pixel values and test results) and store program (software) code executed by the processor 44 to implement functions of the test procedure. These functions may include (i) a graphical user interface (GUI) for communicating with the user and (ii) math functions and look-up functions for processing pixel values to yield oil quality results.

The user interface 43 in this example includes a display 46 (display screen) controlled by a graphical user interface (GUI). The user interface 43 further includes an input device 47, such as a mouse, keypad or touch-screen for inputting user entries.

Examples of the testing device 12 are a mobile (portable) computing device (e.g., smart phone) and a computer, which include all three device components (camera 41, data processing module 42 and user interface 43) in one unitary housing (as one unitary device). The computer may include a program (app) with the software code that implements functions of the test procedure. Similarly, the smart phone may include an app containing the software code that implements functions of the test procedure.

Alternatively, one or more of the device components 41, 42, 43 may be in separate device housings and communicate with each other over wired or wireless communication media. For example, a smart phone may capture the image and then transmit the image's pixel data over a network (e.g., Internet) to a computer (e.g., server) that will perform the processing and reporting. In that case, the software for implementing functions of the test apparatus may be distributed between the computer and the smart phone.

Figure 3:
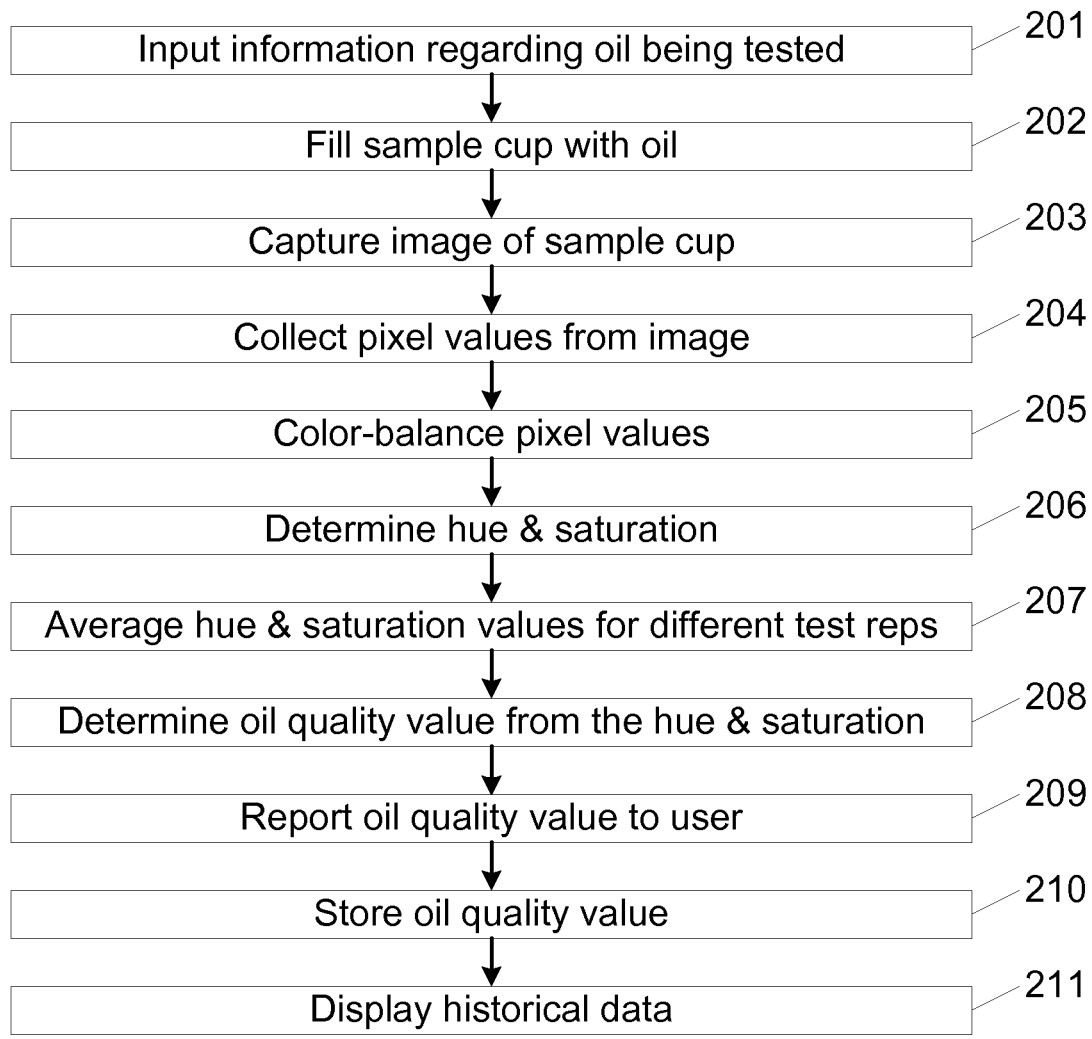
FIG. 3 is a flow chart of example method steps for using the apparatus.

FIG. 3 is a flow chart of example method steps for using the apparatus. The steps of this method are explained as follows, wherein the testing device 12 is exemplified as a smart phone.

In step 201, a user (worker) logs into the app's GUI. The user enters, into the GUI, information about the oil sample to be tested. This information may include an identity (type) of the oil (e.g., a particular corn oil blend), a model number of the frying device that the oil is taken from, an identification of the specific frying device, an identification of the facility, time and date of test, and name of the worker performing the test.

In step 202, oil to be tested is poured into the sample cup's well 30. The oil is preferably filled to the top opening 31 of the cup's well 30. Alternatively, the sample cup 11 is dipped into the oil to be tested. The cup 11 may be placed on a table top. Excess oil, that exceeds the volume of the pocket 30, drains out of the cup through the drain holes 18. This ensures that the cup 11 is filled to the top of the pocket 30, so that all tests are performed with the same height H (FIG. 2D) of oil in the well 30.

Step 203 is an image capture step. As exemplified in FIG. 4, the camera of the smart phone 12 is directed downward toward the top of the sample cup 11. The image in the smart phone camera's viewfinder (smart phone's display) includes an oil sample area 20, the black areas 21, the gray areas 22 and the white areas 23.

Figure 4:
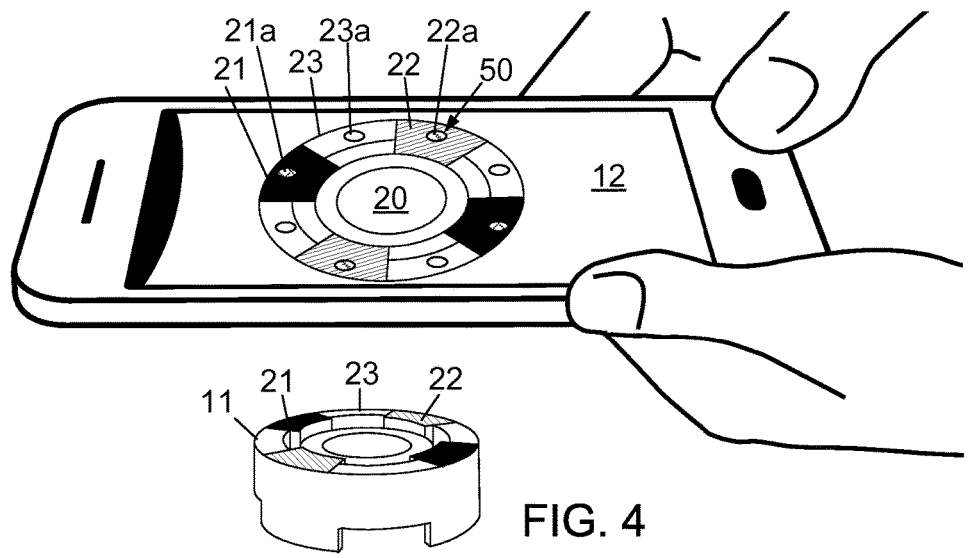
FIG. 4 is a perspective view showing a testing device of the apparatus capturing an image of the sample cup.

As shown in FIG. 4, the software (smart phone app) controls the GUI to display an alignment guide 50 on the smart phone display 51 (camera viewfinder). The alignment guide 50 in this example comprises a circular array of alignment dots 21a, 22a, 23a (alignment marks). Each dot is configured to overlie and be centered on a corresponding one of the calibration areas 21, 22, 23 of the image in the viewfinder when the image 13 is captured (snapshot is taken). The color of each dot 21, 22, 23 may match the color of the corresponding calibration color, such that two dots 21a are black, two dots 22a are gray, and four dots 23a are white. The alignment guide 50 ensures that the image 13 of the cup 11 has a predetermined angular orientation and size, so that the oil and each of the color areas 21, 22, 23 will be in a predetermined location on the captured image frame (screen). The alignment guide 50 also ensures that successive images are taken at a predetermined reproducible distance from the sample, which should render the results more reproducible and reliable.

Step 204 is a pixel data collection step. The processor 44 collects pixel values in each of the four image components (oil, black, gray, white). The pixel values may be taken exclusively from pixels that are within the alignment dots 21a, 22a, 23a. This may eliminate the need for the processor 44 to perform image recognition to decipher which pixels belong to which image components (oil, black area, gray area, white area) of the image. The processor 44 may average the pixel values for each of the four image components (oil, black, gray, white). For example, the black pixel value may be an average from two pixels of the image. The gray pixel value may be an average from two gray pixels of the image. The white pixel value may be an average from four white pixels of the image. The oil pixel value may be an average of multiple (e.g., two or most or all) of the oil pixels.

If multiple (two or more) images of the same sample are captured, the processor 44 may average the pixel values over the multiple images for each of the four image components. This results in four final pixel values respectively for the four image components (oil, black, gray, white), each final value being averaged over multiple pixels and over multiple images for the respective image component.

Step 205 is a color balancing step that corrects the final pixel values based on three preset calibration values. The three calibration values are typically known before the images are captured. In this step, the processor determines an image adjustment (e.g., amount of change) that, if applied to all the pixel values, would convert the pixel value for each calibration color to the predetermined correct calibration value for that calibration color. This adjustment is applied to the oil pixel value to adjust the oil pixel value to a corrected (color-balanced; adjusted) value. This step 205 corrects for errors in image color caused by the illuminating light, and minimizes the influence that the illuminating light would have on the quality results.

In step 206, the processor determines a hue value and a saturation value of the corrected oil pixel value, based on the HSV (hue-saturation-value) system.

Step 207 may be performed if determination of hue and saturation (of step 5) is repeated on different images of the same oil batch. In that case, the resulting hue and saturation may be averaged over the different hue and saturation determinations. Outlier values may be identified and not used (discarded; ignored) in the averages. If too many outliers are identified, the processor may remove all results and start from the beginning.

Figure 5:
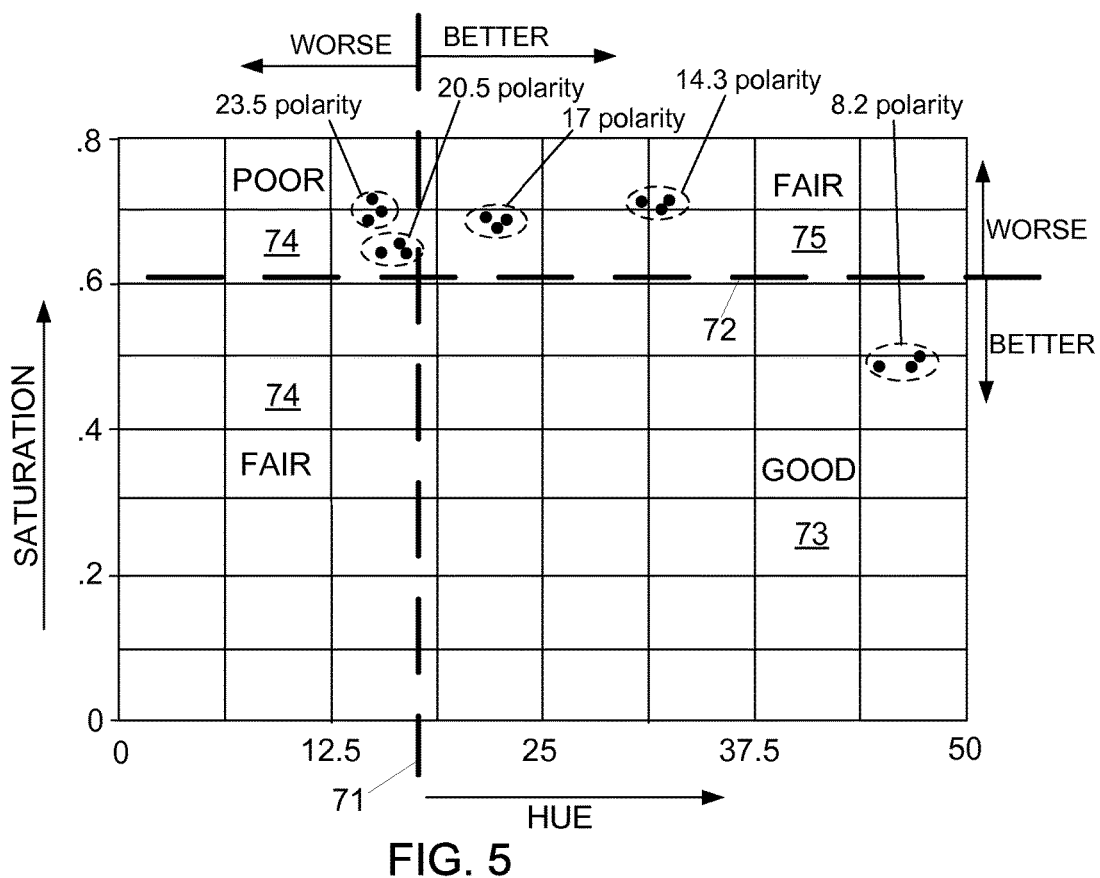
FIG. 5 is a graph of saturation vs. hue for pixels of oil in the captured image.

In step 208, the processor determines the quality of the oil from the hue and the saturation. This step is based on the fact that quality increases with increasing hue and with decreasing saturation. With reference to FIG. 5, the processor 44 compares the measured hue to a hue threshold 71, and compares the saturation to a saturation threshold 72. Hues above the hue threshold are 71 in a better (higher quality) range. Hues below the hue threshold 71 are in a worse (lower quality) range. Saturations below the saturation threshold 72 are in a better (higher quality) range. Saturations above the saturations threshold 72 are in a worse (lower quality) range. The oil's quality may be considered "good" if both hue and saturation are in the better range. The quality may be considered "fair" if one (of hue and saturation) is in the better range and the other is in the worse range. The quality may be considered "poor" ("bad") if both hue and saturation are in the worse range.

In step 209, the processor reports (displays) the oil quality result to the user. The result might include an (i) adjective describing the quality (e.g., "Great", "Fair" or "Poor"), (ii) a recommendation about changing (discarding) the oil, and (iii) an indication (approximation) of what the polarity would be if the oil sample were tested according to ISO 8420. For example, if the result is "good", the GUI may display a message "Great; your oil is in prime condition; do not change the oil; Polarity Range 0%-12%" If the result is "fair", the GUI may display a message "Fair; your oil is in usable condition; you will need to change the oil soon; Polarity Range 12%-18%" If the result is "poor", the GUI may display a message "Poor; your oil is in poor condition; change the oil for best taste; Polarity Range 18% and up"

In step 210, the results of different tests are accumulated (stored) in memory (processor-readable medium) over time. The results may be stored in the testing device's own memory 45 for later lookup. The testing device 12 might transmit, such by Internet 50, the current quality result to a central server 51 (computer). The stored details may include the quality value, raw data (pixel values; hue and saturation) used to obtain the quality value, the identity of the specific fryer (machine) the oil sample was taken from, the date and time of the test, identity of user taking the test, and notes (e.g, observations) the user may have taken.

In step 211, the results over time are presented to the user, for example in the form of a table, a graph or bar graph. The results may be categorized by specific fryer (frying device) of a food preparation facility (e.g., restaurant).

Figure 6:
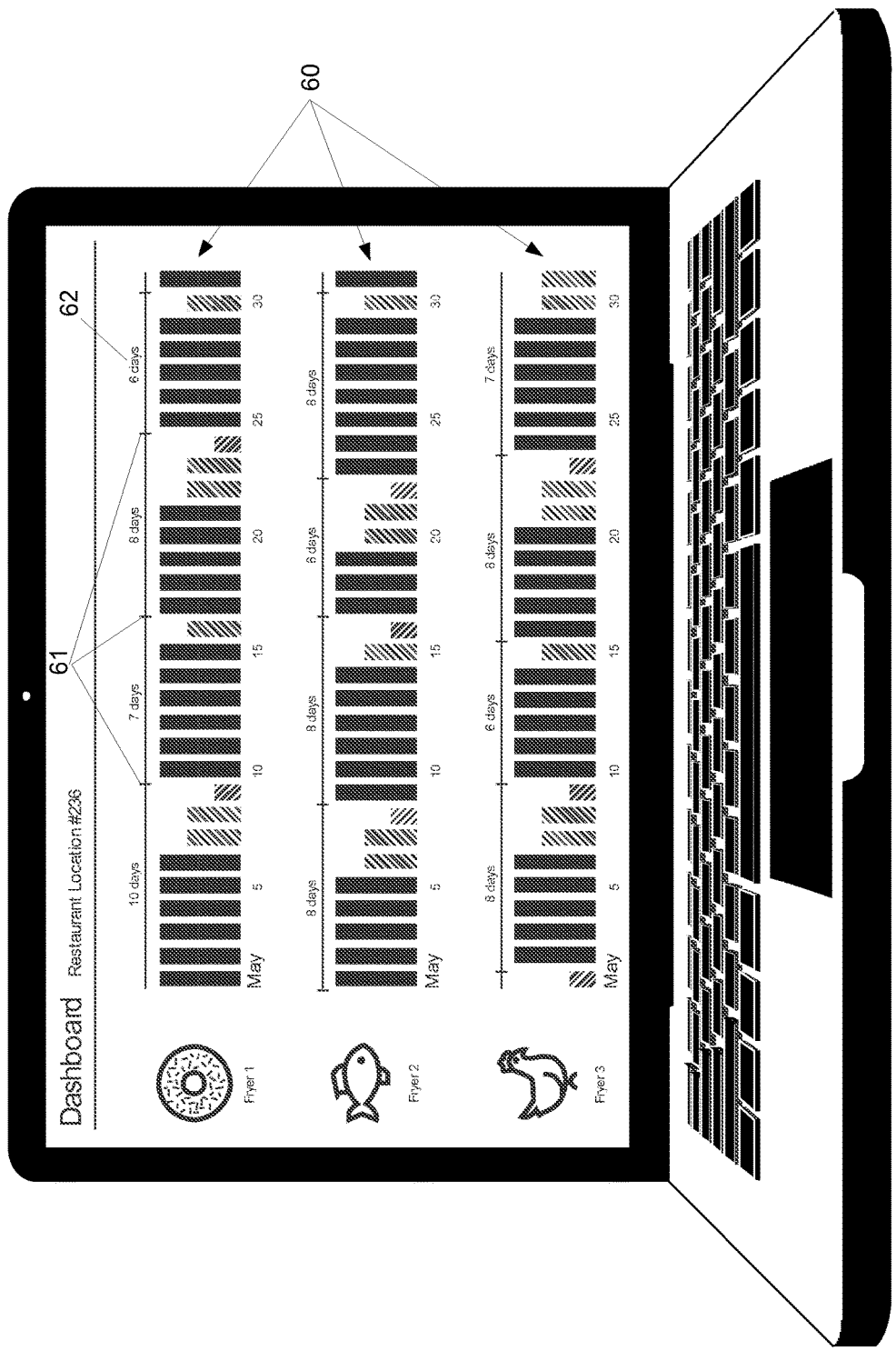
FIG. 6 is an example screenshot of a GUI window displaying bar graphs of oil quality vs. time.

For example, as shown in FIG. 6, the GUI may show different bar graphs 60 for the restaurant's donut fryer, the restaurant's fish fryer and the restaurant's chicken fryer. In the example graph of FIG. 6, one quality result, represented by a vertical bar, is posted for each day. The bar is short for "poor" quality, taller for "fair", and tallest for "good". The color of the bar may vary with results, such as darkest for "poor", lighter for "fair", and lightest for "good". The software in FIG. 6 also assesses, from the historical results, when (what days) degraded oil was replaced with new oil by noting which days the oil quality measurement improved (was better than the previous quality measurement). The GUI in FIG. 6 provides, along each graph 60, markings 61 (in this example horizontal lines bounded by tick marks) that indicate the stretch of time that the same oil has been used and numbers 62 indicating the length of time (how many days) that the stretch of time covers. This historical data may be displayed whenever requested by a user. The historical data may also be displayed at the conclusion of each test when the current test result is displayed. The displayed historical data would include the current test result.

The computing device that performs step 210-211 (accumulation and presentation of historical data) may be the same computing device as or a different computing device than the computing device 12 that processed the pixel data to determine the quality result. Each worker of a food preparation institution (e.g., restaurant, factory) may obtain oil quality results (via steps 201-209) using his/her own smart phone, with the results from all workers being uploaded to the central computer 51 (server) that performs steps 210-211 (accumulation and presentation of historical data).

The procedure described above uses three calibration colors to obtain accurate results in correcting the oil pixel value. Alternatively, only one or two calibration colors might be satisfactory. And more than three calibration colors may be used, to yield more accurate results.

The procedure described above distinguishes between three levels of quality (good, fair, poor). Alternatively, the procedure might distinguish between two levels. Or it might distinguish between more than three levels, which may entail using two or more hue thresholds and thus three or more hue ranges. Or using two or more saturation thresholds and thus three or more saturation ranges.

The procedure might also determine (calculate) a numeric value of quality as a function of hue and saturation. The function might be positively related to a weighted sum of hue and saturation, such as the equation: polarity=A*hue+B*saturation. The values of A and B might be determined through statistical analysis (e.g., least squares analysis; linear regression) of polarity versus hue and saturation. Using this equation in a test, the processor would approximate the polarity from the measured hue and saturation, and report (display) the approximated polarity to the user. Alternatively, the approximate polarity might be calculated as a function of only hue and not saturation.

The aforementioned hue and saturation thresholds and the aforementioned coefficients A and B may be specific for a specific set of conditions, where "set of conditions" may include to a specific type of oil, a specific fried food type, and/or a specific type or model of fryer. The specific (particular) type of oil may correspond to a specific oil formulation or specific (particular) oil blend associated with a particular food service company. Accordingly, the determination of quality or polarity of an oil being tested might use the thresholds or equation that were derived using oil of the specific conditions (e.g., same oil type) as the oil being tested.

The procedure described above includes different possible averaging stages (e.g., averaging over pixels within an image and averaging over different images, and averaging over different samples). However, one or more or all of these averaging stages may be omitted.

An example procedure for determining the thresholds 71, 72 (FIG. 5) is as follows: Oil of a specific set of conditions (e.g., specific type of oil, specific type of fried food, specific type of fryer, specific fryer model) is periodically sampled as it degrades over time. Each sample is tested to obtain its polarity, such as by performing a ISO 8420 test or by using a Testo oil tester. Each sample is also tested via steps 202-206 to obtain its hue and saturation. Example correspondences of polarity, hue and saturation for particular batch of oil are shown in Table 1. Table 1 represents five samples that were taken from the same batch of oil at five respective ages, and each sample was tested three times (three reps) for hue and saturation.

TABLE 1

Test Results of Polarity, Hue & Saturation for a Batch of Oil at Different Ages

| | Polarity | | | | |
|---|---|---|---|---|---|
| | 8.2 | 14.3 | 17 | 20.5 | 23.5 |
| Rep 1: Hue/Sat | 46.8/0.485 | 30.9/0.714 | 22.4/0.678 | 17.0/0.643 | 14.8/0.685 |
| Rep 2: Hue/Sat | 47.3/0.501 | 32.1/0.703 | 21.7/0.693 | 15.6/0.645 | 15.0/0.717 |
| Rep 3: Hue/Sat | 44.9/0.487 | 32.5/0.716 | 22.9/0.689 | 16.6/0.655 | 15.5/0.700 |

Saturation is graphed versus hue, as shown in FIG. 5. The horizontal saturation threshold line 71 and the vertical hue threshold line 72 are drawn, splitting the graph into four regions 73, 74, 75, 76. The locations of the threshold lines 71, 72 are selected to render (i) data points of good polarities in one region 73, (ii) data points of poor polarities in a diagonally opposite region 74, and (iii) data points of fair polarities in the remaining two regions 75, 76. It is preferable that the thresholds (used in determining quality of a sample oil) be derived using oil of the same blend as that of the sample oil.

Figure 7:
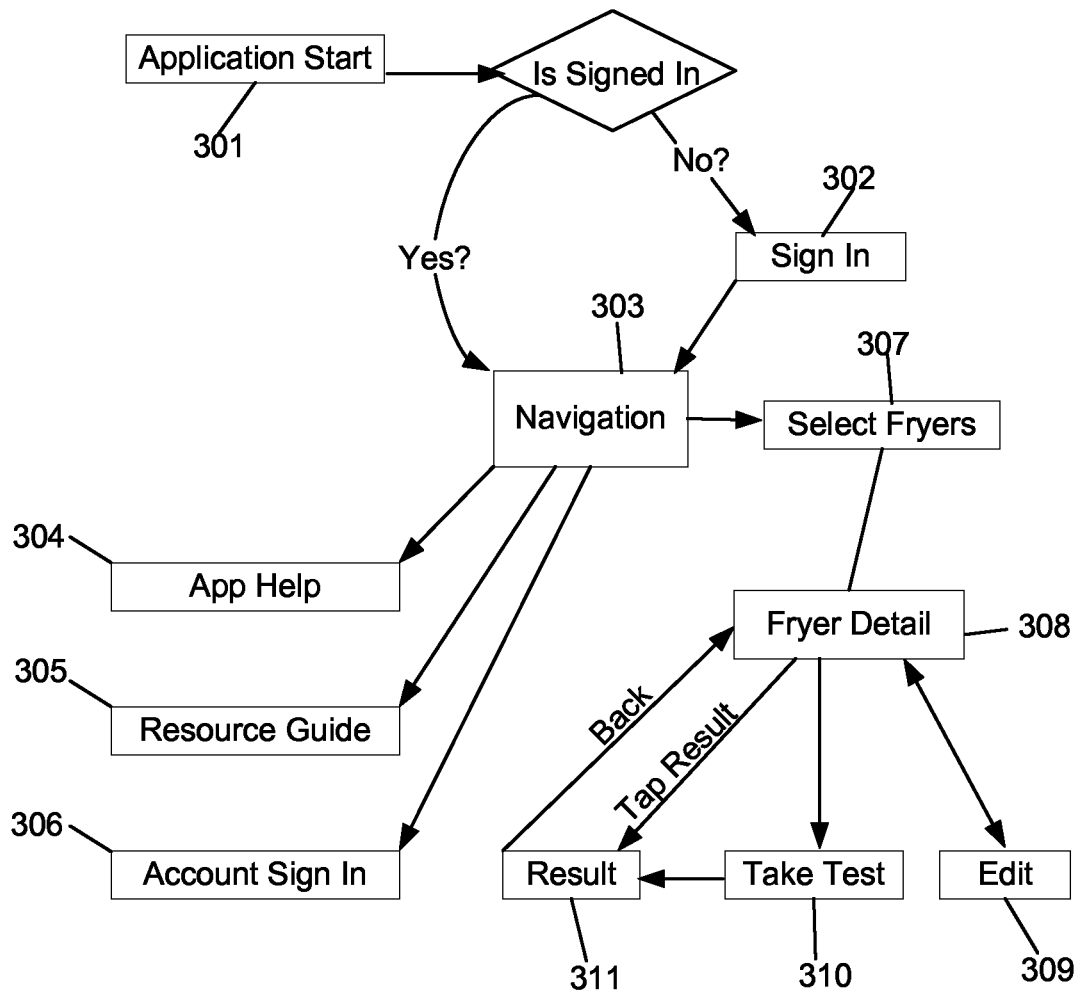
FIG. 7 is a flow chart of a procedure for navigating windows of the GUI.
Figure 8:
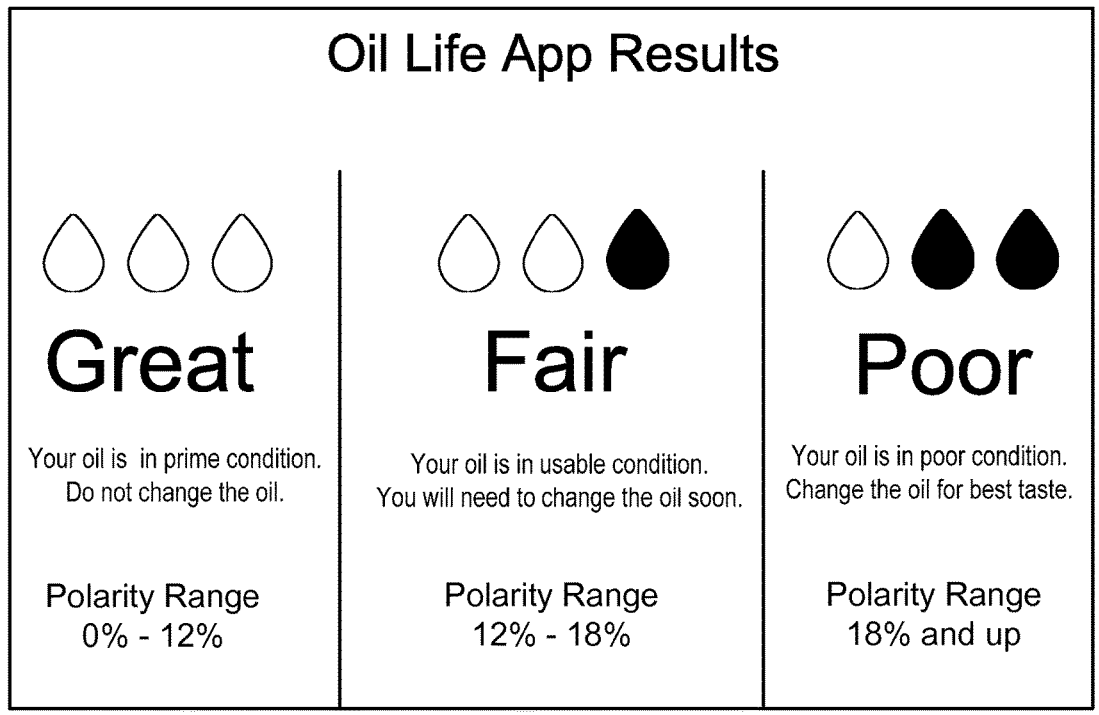
FIG. 8 is a screenshot of an example App Help window of the GUI.

FIG. 7 is a flow chart of a procedure for using the GUI when performing a test. A user opens the app (program) 301. The user signs in 302 if not already signed it. The sign-in enables the user to use functionality of the testing app (program). From a general menu window 303, the user may call up different windows. One window that may be called up is an App Help window 304, exemplified in FIG. 8, which might be on the user's smart phone. This window 304 provides cursory educational information about the implications of different polarity ranges and oil qualities. Another window that may be called up is a Resource Guide 305, which provides detailed information (instructions) about using the apparatus. Another window that may be called up is an Account Sign In window 306, through which the user signs in to an external server. This is the server that uploads the test data from the testing device and provides, to the user, historical oil-quality results collected from all workers at other facilities. Another window that can be called up is a test initiation window 307. Through this test initiation window, the user selects a specific fryer whose oil is to be tested, enters details about the fryer 308, edits those details 309, initiates the test procedure 310 (steps 202-208), and sees the results 311 (steps 209, 211).

Figure 9:
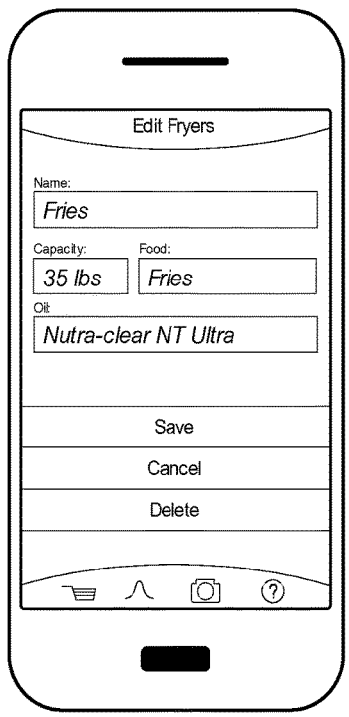
FIG. 9 is an screenshot of an example GUI window for adding a new fryer to a database of the apparatus.

FIG. 9 shows an example GUI window, in this example on a smart phone, through which a user may add a new fryer to the database and edits information to the database about fryers already in the database. In this example, the fryer model is a "Nutra-clear NT Ultra" with a 35 lb capacity, and is being used to fry "fries".

Figure 10:
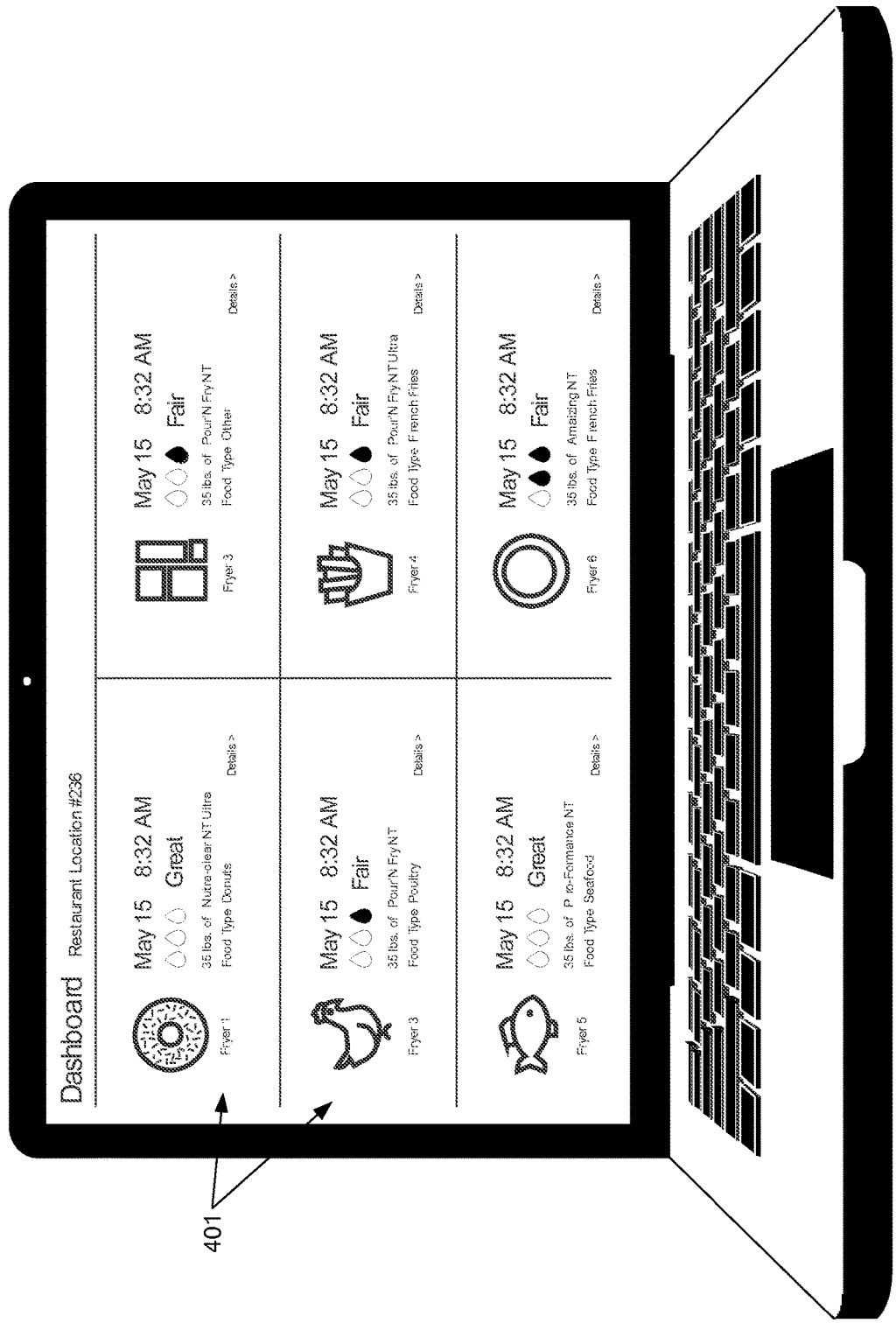
FIG. 10 is a screenshot of an example GUI window for displaying historical oil-quality results.

FIG. 10 shows a GUI window for displaying historical quality results. This window may be on a computer that collects test results from different workers' handheld testing devices. This window has different sections 401. Each section 401 displays the latest results for a respective fryer. User-selection (e.g., by touching or clicking) of any one of the sections 401 yields more historical data about that selected fryer, such as in the form of one of the bar graphs of FIG. 6.

The components and procedures described above provide examples of elements recited in the claims. They also provide examples of how a person of ordinary skill in the art can make and use the claimed invention. They are described here to provide enablement and best mode without imposing limitations that are not recited in the claims. In some instances in the above description, a term is followed by a substantially equivalent term enclosed in parentheses.

The invention claimed is:

1. A processor-implemented method of providing an oil-quality indication, comprising:
   capturing an image using a camera of a portable user device;
   receiving image data associated with the captured image, wherein the image data includes (i) oil sample pixels which are associated with an oil sample and (ii) calibration color pixels which are associated with a calibration color;
   adjusting the oil sample pixels based on the calibration color pixels;
   determining a saturation value and a hue value based on the adjusted oil sample pixels;
   determining an oil quality value based on the saturation value and the hue value; and
   storing the oil quality value in a non-transitory processor-readable medium.

2. The method of claim 1, further comprising:
   approximating a polarity of the oil sample based on the saturation value and the hue value.

3. The method of claim 1, wherein determining of the oil quality value comprises:
   determining whether the saturation value falls within a predetermined saturation low quality range;
   determining whether the hue value falls within a predetermined low quality hue range; and
   assigning a low quality value for the oil quality value when the saturation value falls within the predetermined low quality saturation range and the hue value falls within the predetermined low quality hue range.

4. The method of claim 3, wherein the oil sample is associated with a particular oil formulation, and wherein the predetermined low quality saturation range and the predetermined low quality hue range are associated with the particular oil formulation.

5. The method of claim 4, wherein different predetermined low quality ranges are respectively associated with different oil formulations.

6. The method of claim 4, wherein the particular oil formulation is an oil blend associated with a particular food service company.

7. The method of claim 3, further comprising:
   determining the predetermined low quality saturation range and the predetermined low quality hue range based on captured images of hue values and saturation values of oil of a same type as the oil sample having known polarity values.

8. The method of claim 1, further comprising storing the oil quality value with previous oil quality metric values in the processor-readable data store.

9. The method of claim 8, further comprising displaying an indication of the oil quality value on a graphical user interface.

10. The method of claim 9, further comprising displaying indications of the oil quality value and the previous oil quality metric values simultaneously on the graphical user interface.

11. The method of claim 9, wherein the indication identifies a quality of the oil sample as one of two or one of three available quality states.

12. The method of claim 9, wherein the indication identifies whether oil associated with the oil sample should be discarded.

13. The method of claim 1, wherein the oil quality value is stored with an indication of a particular machine from which the oil sample was taken.

14. The method of claim 1, wherein adjusting the pixels comprises:
   determining an amount of change to the calibration color pixels necessary to equalize the calibration color pixels to a present value;
   adjusting the pixels associated with the oil sample based on the amount of change.

15. The method of claim 1, wherein pixels associated with a second calibration color are received, wherein the pixels associated with the oil sample are further adjusted based on the pixels associated with the second calibration color.

16. The method of claim 1, wherein the calibration color is one of white, black, and gray.

17. The method of claim 1, wherein image data associated with multiple captured images of the oil sample is received, wherein the saturation value and the hue value are based on the image data associated with the multiple captured images.

18. The method of claim 1, further comprising ignoring a pixel associated with the oil sample significantly differs from others of the pixels associated with the oil sample.

19. The method of claim 1, wherein the captured image is taken using a portable device application.

20. The method of claim 1, wherein the captured image is a image of an oil sample device, wherein the oil sample device includes a cup for holding the oil sample and the calibration color.

21. The method of claim 20, wherein the calibration color is a predetermined color.

22. The method of claim 21, wherein the oil sample device includes one or more drain holes surrounding the cup, wherein the calibration color at least partially surrounds the cup and the one or more drain holes.

23. The method of claim 22, wherein multiple calibration colors, including the calibration color, surround the cup and the one or more hole regions.

24. The method of claim 21, further comprising:
providing a user interface for capturing the captured image, wherein the user interface includes a guide for aligning the calibration color of the oil sample device with a camera.

25. A processor-implemented system for providing an oil-quality indication, comprising:
an oil sample device comprising a cup and an area of a calibration color;
a mobile device application configured to:
receive image data associated with a captured image of an oil sample in the cup, wherein the image includes oil sample pixels associated with the oil sample and calibration color pixels associated with the area of the calibration color;
adjust the oil sample pixels based on the calibration color pixels;
determine a saturation value and a hue value based on the adjusted oil sample pixels;
determine an oil quality value based on the saturation value and the hue value; and
store the oil quality value in a non-transitory processor-readable medium; and
display an indication of a quality of the oil sample on a user interface of the mobile device application.

26. The system of claim 25, wherein the application is further configured for:
approximating a polarity of the oil sample based on the saturation value and the hue value.

27. The system of claim 25, wherein determining of the oil quality value comprises:
determining whether the saturation value falls within a predetermined saturation low quality range;
determining whether the hue value falls within a predetermined low quality hue range; and
assigning a low quality value for the oil quality value when the saturation value falls within the predetermined low quality saturation range and the hue value falls within the predetermined low quality hue range.

28. The system of claim 27, wherein the oil sample is associated with a particular oil formulation, and wherein the predetermined low quality saturation range and the predetermined low quality hue range are associated with the particular oil formulation.

29. The system of claim 28, wherein different predetermined low quality ranges are respectively associated with different oil formulations.

30. The system of claim 28, wherein the particular oil formulation is an oil blend associated with a particular food service company.

31. The system of claim 27, wherein the application is further configured for:
determining the predetermined low quality saturation range and the predetermined low quality hue range based on captured images of hue values and saturation values of oil of a same type as the oil sample having known polarity values.

32. The system of claim 25, wherein the application is further configured for storing the oil quality value with previous oil quality metric values in the processor-readable data store.

33. The system of claim 32, wherein the application is further configured for displaying an indication of the oil quality value on a graphical user interface.

34. The system of claim 33, wherein the application is further configured for displaying indications of the oil quality value and the previous oil quality metric values simultaneously on the graphical user interface.

35. The system of claim 33, wherein the indication identifies a quality of the oil sample as one of two or one of three available quality states.

36. The system of claim 33, wherein the indication identifies whether oil associated with the oil sample should be discarded.

37. The system of claim 25, wherein the oil quality value is stored with an indication of a particular machine from which the oil sample was taken.

38. The system of claim 25, wherein adjusting the pixels comprises:
determining an amount of change to the calibration color pixels necessary to equalize the calibration color pixels to a present value;
adjusting the pixels associated with the oil sample based on the amount of change.

39. The system of claim 25, wherein pixels associated with a second calibration color are received, wherein the pixels associated with the oil sample are further adjusted based on the pixels associated with the second calibration color.

40. The method of claim 25, wherein the calibration color is one of white, black, and gray.

41. The system of claim 25, wherein image data associated with multiple captured images of the oil sample is received, wherein the saturation value and the hue value are based on the image data associated with the multiple captured images.

42. The system of claim 25, wherein the application is further configured for ignoring a pixel associated with the oil sample significantly differs from others of the pixels associated with the oil sample.

43. The system of claim 25, wherein the captured image is taken using a portable device application.

44. The system of claim 25, wherein the captured image is a image of an oil sample device, wherein the oil sample device includes a cup for holding the oil sample and the calibration color.

45. The system of claim 44, wherein the calibration color is a predetermined color.

46. The system of claim 45, wherein the oil sample device includes one or more drain holes surrounding the cup, wherein the calibration color at least partially surrounds the cup and the one or more drain holes.

47. The system of claim 46, wherein multiple calibration colors, including the calibration color, surround the cup and the one or more hole regions.

48. The system of claim 45, wherein the application is further configured for:

provided a user interface for capturing the captured image, wherein the user interface includes a guide for aligning the calibration color of the oil sample device with a camera.

* * * * *